(12) United States Patent
Fateh et al.

(10) Patent No.: US 10,319,473 B2
(45) Date of Patent: Jun. 11, 2019

(54) WEARABLE SYSTEM FOR HEALTHCARE MANAGEMENT

(71) Applicant: Kali Care, Inc., Mountain View, CA (US)

(72) Inventors: Sina Fateh, Mountain View, CA (US); Navid Nick Afsarifard, Atherton, CA (US)

(73) Assignee: KALI CARE, INC., Mountain View, CA (US)

(*) Notice: Subject to any disclaimer, the term of this patent is extended or adjusted under 35 U.S.C. 154(b) by 568 days.

(21) Appl. No.: 15/098,208

(22) Filed: Apr. 13, 2016

(65) Prior Publication Data

US 2016/0306932 A1    Oct. 20, 2016

Related U.S. Application Data

(60) Provisional application No. 62/150,196, filed on Apr. 20, 2015.

(51) Int. Cl.
*G06F 3/01* (2006.01)
*G06F 19/00* (2018.01)
(Continued)

(52) U.S. Cl.
CPC .......... *G16H 10/65* (2018.01); *G06F 3/014* (2013.01); *G06F 3/017* (2013.01);
(Continued)

(58) Field of Classification Search
None
See application file for complete search history.

(56) References Cited

U.S. PATENT DOCUMENTS 9,289,603 B1 * 3/2016 Giuffrida .............. A61B 5/1101
2003/0184575 A1 * 10/2003 Reho ....................... A61B 5/742
715/714

(Continued)

FOREIGN PATENT DOCUMENTS

| WO | 2012101093 A2 | 8/2012 |
| WO | 2014040023 A1 | 3/2014 |

OTHER PUBLICATIONS

International Search Report and Written Opinion dated Aug. 11, 2016 for International Application No. PCT/US2016/028377, 7 pages.

*Primary Examiner* — Neal Sereboff
(74) *Attorney, Agent, or Firm* — Perkins Coie LLP

(57) ABSTRACT

Various of the disclosed embodiments enable adherence to a medication regimen or a healthcare regimen to be monitored using a wearable system. The wearable system can be used to monitor a user's activities by recording activities using a camera that is placed at the anterior part of the user's wrist. The camera, or another sensor, can detect, identify, and verifying movements or gestures of the hand or fingers. A gesture may be a particular hand position, finger movement, or combination of finger movements that are indicative of performance of an activity required as part of a medication or healthcare regimen. The camera can generate a recording of an activity, and the wearable system or a distinct computing device can then analyze the recording and determine compliance to the medication or healthcare regimen based on what action(s), if any, were identified in the recording.

8 Claims, 17 Drawing Sheets

(51) Int. Cl.
*G16H 10/65* (2018.01)
*H04N 5/225* (2006.01)

(52) U.S. Cl.
CPC ....... *G06F 19/3456* (2013.01); *H04N 5/2257* (2013.01); *G06F 2203/011* (2013.01)

(56) References Cited

U.S. PATENT DOCUMENTS

| | | | |
|---|---|---|---|
| 2013/0336519 A1* | 12/2013 | Connor | G06K 9/00771 |
| | | | 382/100 |
| 2014/0278220 A1* | 9/2014 | Yuen | G01B 21/16 |
| | | | 702/150 |
| 2014/0350353 A1* | 11/2014 | Connor | A61B 5/4866 |
| | | | 600/301 |
| 2017/0011210 A1* | 1/2017 | Cheong | A61B 5/0022 |

\* cited by examiner

WEARABLE SYSTEM FOR HEALTHCARE MANAGEMENT

CROSS-REFERENCE TO RELATED APPLICATIONS

This application claims priority to and the benefit of U.S. Provisional Application 62/150,196, entitled "WEARABLE SYSTEM FOR HEALTHCARE MANAGEMENT" filed on Apr. 20, 2015.

RELATED FIELD

Various embodiments concern medication and healthcare management. More specifically, various embodiments relate to wearable systems and methods for monitoring adherence to a medication regimen or a healthcare regimen.

BACKGROUND

Approximately thirty percent of medication prescriptions are never filled, and approximately fifty percent of medications for chronic disease are not taken as prescribed. This lack of adherence to medication regimens has dramatic effects on the health of individuals and healthcare costs for society as a whole. Non-adherence has been estimated to cost the U.S. health care system $200 billion annually.

For example, compliance with an ophthalmological medication plan (also referred to as a "medication regimen") may be vital for preventing visual loss and blindness resulting from chronic conditions such as glaucoma. However, almost seventy-five percent of patients admit to some form of noncompliant behavior, over thirty percent do not fill their prescriptions, and nearly fifty percent discontinue their prescriptions within six months.

While forgetfulness is one barrier to medication adherence, it is not the only barrier. Taking the medication at the wrong time, stopping a medication regimen too early, and taking the wrong dose also represent serious barriers. Unfortunately, there are no effective systems for managing adherence to a medication regimen that may be necessary for maintaining or improving an individual's health.

BRIEF DESCRIPTION OF THE DRAWINGS

Numerous embodiments of the present invention are illustrated by way of example and not limitation in the accompanying drawings, in which like references indicate similar elements.

Figure 1:
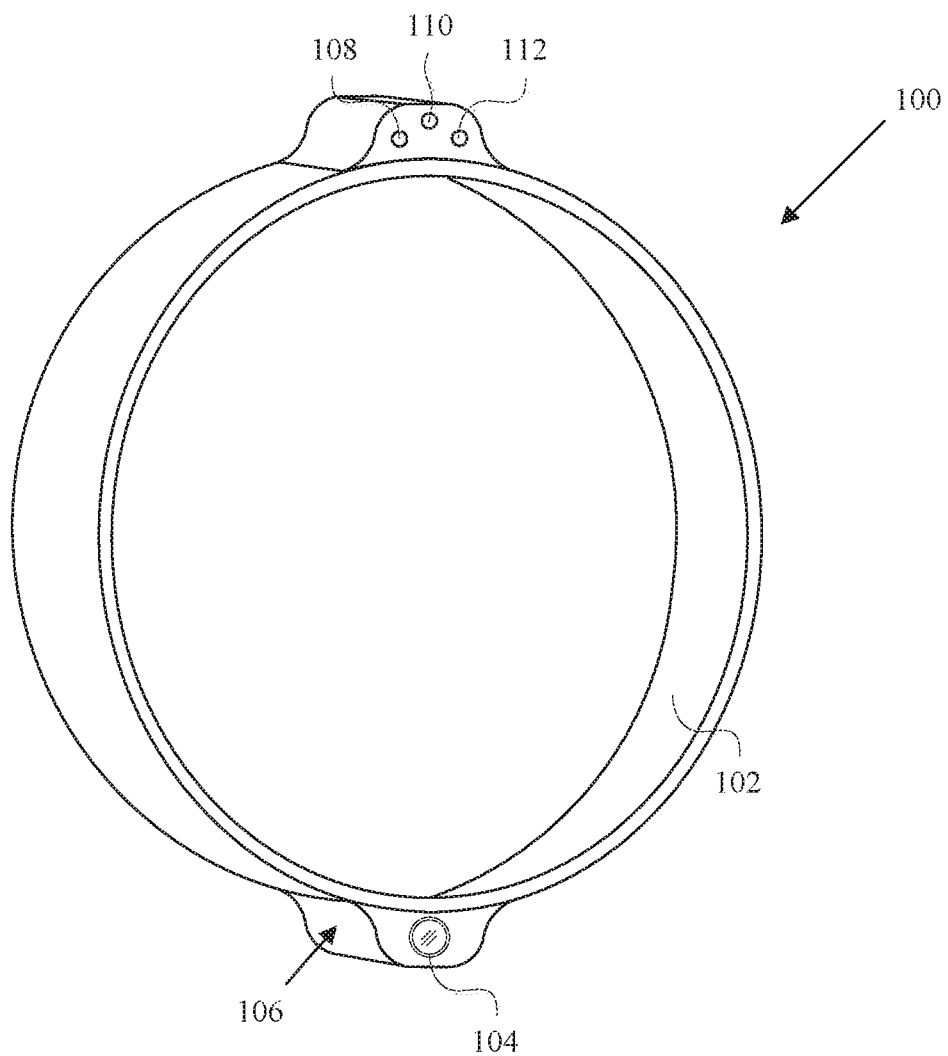
FIG. 1 is a perspective view of a wearable system according to various embodiments.

The figures depict various embodiments that are described throughout the Detailed Description for purposes of illustration only. While specific embodiments have been shown by way of example in the drawings and are described in detail below, the invention is amenable to various modifications and alternative forms. The intention is not to limit the invention to the particular embodiments described. Accordingly, the claimed subject matter is intended to cover all modifications, equivalents, and alternatives falling within the scope of the present invention as defined by the appended claims.

DETAILED DESCRIPTION

Various embodiments generally relate to healthcare management and, more specifically, to wearable systems and methods for monitoring adherence to a medication regimen or a healthcare regimen. The systems and methods described herein are able to monitor adherence by tracking movement of the user's hand and/or fingers. A medication regimen is a plan that includes medication activities designed to improve or maintain the health status of a person. For example, a medication regimen can identify a medication that a patient is to administer, the time and/or frequency at which a dose of medication is to be administered, the amount or quantity of each dose of medication, a duration of time (e.g., start time, end time) over which a medication is to be taken, etc. A healthcare regimen is a plan that includes healthcare activities designed to improve or maintain the health status of a person. For example, a healthcare regimen may instruct a patient to measure blood pressure or pulse rate at a certain time interval (e.g., daily). As another example, a healthcare regimen may require that the patient perform a certain exercise one or more times per day. While the Detailed Description may only refer to one of a medication regimen or a healthcare regimen in various instances, one skilled in the art will recognize the systems and methods described herein can be used to monitor adherence to either a medication regimen or a healthcare regimen unless otherwise specified.

There are many reasons why an individual may not adhere to or comply with a medication regimen. For example, the individual may forget to take the medication, misunderstand the regimen, make an error regarding the dosage (e.g., amount, quantity, time), forget to refill a prescription, or could simply be unable to afford the medication. The lack of adherence may have a severe impact on the individual's health. Furthermore, there may be a number of interested parties who have a vested interest in whether the individual adheres to a medication regimen, such as the individual him or herself, family members, healthcare personnel (e.g., physician, nurse, pharmacist), researchers, etc. For example, a child of an elderly parent may want to know when the parent fails to adhere to a prescribed medication regimen so the child can identify the reason(s) for the non-adherence and take appropriate action(s).

One of the most important ways in which a person interacts with the environment is through the hands. In fact, one or both hands typically must be used in order to satisfy the obligations of a medication or healthcare regimen. Hand-eye coordination is essential to accurately detecting, guiding, reaching, and grasping objects of interest (e.g., a bottle of medication). But hand-eye coordination is a sophisticated and fast process that involves various biological systems, including the visual system, the sensory system, and the motor system.

Various embodiments described herein enable adherence to a medication or healthcare regimen to be monitored and/or managed for an individual (who may also be referred to as a "user" of the systems described herein) by placing a camera, image sensor, depth sensor, etc., within the anterior region of the user's wrist. While cameras or sensors may also be placed elsewhere around the wrist, the anterior region provides a superior point of view for detecting, identifying, and verifying movement of the hand, fingers, or any objects grasped by the hands or fingers. Objects of interest may include medications, medication containers, tools (e.g., surgical instruments, insulin pens, epinephrine injectors), food, electronic devices (e.g., cellular phones, glucose meters), etc.

The camera, sensors, etc., can be used to generate a recording of an activity involving the user's hand(s) and/or fingers. The recording can be analyzed to determine what activity (e.g., physical movement, position) caused the recording to be generated. For example, a camera may generate a visual recording (e.g., a photograph or video) in response to detecting an event (e.g., performance of a particular gesture or being brought within proximity to a bottle of medication) that indicates medication is likely to be dispensed or administered. Relevant gestures may include a particular hand position, a particular finger or arm movement or a combination of movements, etc. As another example, a sound sensor (e.g., microphone) may generate an audio recording in response to sensing one or more particular sounds (e.g., a vocal command, the opening of blister pack, or the depression of an inhaler) that indicate medication is likely to be dispensed or administered.

In some embodiments, an administrator provides control data that identifies spatial tendencies associated with a particular user. The term "administrator" may refer to an individual or a computing device. Each of the spatial tendencies corresponds to at least one particular action. Recordings can be analyzed (e.g., by a wearable system or a distinct computing device) to identify spatial flags that are present in the recordings. The spatial flags can be unique movements, positions, gestures, etc. The spatial flags can be compared to the spatial tendencies to determine whether the recording represents the particular user performing a particular action (e.g., administering medicine or using a glucose meter) that is required as part of a medication or healthcare regimen.

Other sensors can be used to track movement of the wearable system, movement or position of the user's hand(s) and fingers, ambient conditions, etc. For example, the wearable system may include an electromagnetic sensor, motion sensor, positional sensor, sound sensor, climate (e.g., humidity, temperature) sensor, or a pressure sensor. One or more of the sensors may be configured to activate the camera, generate and transmit relevant data to a distinct computing device, sync with a remote storage, etc.

The recordings and associated data (e.g., spatial flags, metadata) can be used to track a user's adherence to a medication or healthcare regimen and then generate an adherence report. In some embodiments, the user is able to view the adherence report, as well as any recording(s) or other data, via an electronic display communicatively coupled to the wearable system. The user and other interested parties (e.g., family member, physician, pharmacist) may also view the recording(s), data, and/or adherence report via a distinct display device that is configured to receive information from the wearable system from across a network (e.g., the Internet, a Bluetooth connection, or a cellular network). For example, an application may be configured to present portions of various records and the adherence report to an interested party on a cellular phone, tablet, laptop computer, etc.

For the purposes of explanation, numerous specific details are set forth below in order to provide a thorough understanding of various embodiments. However, it will be apparent to one skilled in the art that the embodiments may be practiced without some or many of these specific details. While embodiments are described for convenience with reference to monitoring participation in activities associated with medication regimens and healthcare regimens, various embodiments are equally applicable to monitoring other activities, both within and outside the medical industry. For example, some embodiments of the wearable system described herein can be used to monitor surgical techniques of physicians, manufacturing techniques of hardware assemblers and automotive service technicians, etc.

TERMINOLOGY

Brief definitions of terms, abbreviations, and phrases used throughout the specification are given below.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments necessarily mutually exclusive of other embodiments. Moreover, various features are described that may be exhibited by some embodiments and not by others. Similarly, various requirements are described that may be requirements for some embodiments and not for other embodiments.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of or connection between the elements can be physical, logical, or a combination thereof. For example, two components may be coupled directly to one another or via one or more intermediary channels or components. As another example, devices may be coupled in such a way that information can be passed there between, while not sharing any physical connection with one another. Additionally, the words "herein," "above," "below," and words of similar import, when used in this application, shall refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

If the specification states a component or feature "may," "can," "could," or "might" be included or have a characteristic, that particular component or feature is not required to be included or have the characteristic.

The term "module" refers broadly to software, hardware, or firmware components. Modules are typically functional components that can generate useful data or other output using specified input(s). A module may or may not be self-contained. An application program (also called an "application") may include one or more modules, or a module can include one or more application programs.

The terminology used in the Detailed Description is intended to be interpreted in its broadest reasonable manner, even though it is being used in conjunction with certain examples. The terms used in this specification generally have their ordinary meanings in the art, within the context of the disclosure, and in the specific context where each term is used. For convenience, certain terms may be highlighted, for example using capitalization, italics, and/or quotation marks. The use of highlighting has no influence on the scope and meaning of a term; the scope and meaning of a term is the same, in the same context, whether or not it is highlighted. It will be appreciated that an element or feature can be described in more than one way.

Consequently, alternative language and synonyms may be used for any one or more of the terms discussed herein, and special significance is not to be placed on whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to the various embodiments given in this specification.

System Overview

FIG. 1 is a perspective view of a wearable system 100 according to various embodiments. The wearable system 100 can include a wristband 102, a camera 104, an electronics compartment 106, an electromagnetic sensor 108, a motion sensor 110, a positional sensor 112, or some combination thereof. The wristband 102 may be made of metal, an elastomer material, or any suitable material that is durable and can be worn around the user's wrist. For example, a flexible, water-resistant rubber wristband may be used that can be worn throughout the day (e.g., while sleeping and showering). In some embodiments the wristband 102 is sufficiently flexible to stretch around the user's hand, while in other embodiments the wristband 102 includes a clasp that allows the wristband 102 to be secured around the user's wrist. The clasp (or another suitable attachment mechanism such as a buckle or snap fastener) allows the wristband 102 to be adjusted around the user's wrist. For example, a stainless steel fold-over clasp may be connected to the wristband 102 that allows the user to easily remove the wristband 102 if necessary.

The camera 104 can be used to visually record activities involving the user's hand, fingers, or both. For instance, the camera 104 may capture images and/or video. In various embodiments, the camera 104 is coupled to the wristband 102 in an anterior region of the wrist and oriented toward the user's hand. The camera 104 may be configured to record medication management activities, such as opening a container of medicine, dispensing medicine, administering medicine, etc. The camera 104 can also be configured to record healthcare management activities, such as taking a diagnostic image or using a glucose meter, blood pressure monitor, cholesterol monitor, spirometer, pulse oximeter, thermometer, etc. One skilled in the art will recognize that a particular camera 104 may be configured to record all possible activities or some subset of these activities. Additionally or alternatively, a depth sensor or an image sensor (e.g., configured for thermal imaging, radar, or sonar) may be used to discover characteristics of the ambient environment.

The wearable system 100 can also include an electronics compartment 106 that includes some combination of a processor, storage medium, power supply, communication module, etc. As will be discussed below with respect to FIG. 2B, various components of the electronics compartment 106 assist in generating and analyzing recordings.

In some embodiments, the wearable system 100 also includes one or more sensors, such as an electromagnetic sensor 108, a motion sensor 110, a positional sensor 112, etc. The electromagnetic sensor 108 can be configured to detect and identify variations in electromagnetic radiation in the ambient environment. For example, the electromagnetic sensor 108 may be configured to detect variations in infrared radiation, ultraviolet radiation, radio waves, etc. The sensors may also be used to activate and deactivate the camera 104, transmit data signals to a computing device, or synchronize any stored data (e.g., recordings) with a remote storage. For example, the camera 104 could be activated in response to the electromagnetic sensor 108 determining the variation in electromagnetic radiation has exceeded a specific threshold. Further yet, the camera 104 may be configured to activate when the motion sensor 110 detects a particular motion or set of motions, which can also be referred to as a "gesture." The gesture (e.g., shaking a hand, rotating wrist, or tapping a surface a certain number of times) may be a default gesture input by an administrator or a personalized gesture input by the user. The camera 104 may also be activated and deactivated in other ways, such as an on/off button, vocal activation (e.g., via speaker 424 of FIG. 4A), sensing of pressure (e.g., via pressure sensors 430 of FIG. 4C), sensing of a radio-frequency identification (RFID) signature, etc.

While the sensors (e.g., electromagnetic sensor 108, motion sensor 110, and positional sensor 112) are illustrated as being located in the posterior region of the wrist opposite the camera, one skilled in the art will recognize the sensors could be coupled to the wristband 102 in any location. For example, the electromagnetic sensor 108 may be located adjacent to the camera 104 in the anterior region of the wrist, while the motion sensor 110 remains in the posterior region. It may be desirable for certain sensors (e.g., the electromagnetic sensor 108 or positional sensor 112) to be located in proximity to the camera 104.

Although the wearable system 100 is described and illustrated as a self-contained apparatus, one skilled in the art will recognize that the same features could also be implemented via attachments to conventional apparatuses designed to be worn around the user's wrist. For example, a camera accessory for monitoring user compliance with a medication or healthcare regimen could be attached to a medical ID bracelet, Fitbit fitness tracker, Apple Watch, or a conventional watch. The camera accessory may utilize functionalities supported by the device to which it is attached (e.g., the transmission and reception capabilities of an Apple Watch) or could be entirely self-contained.

Figure 2A:
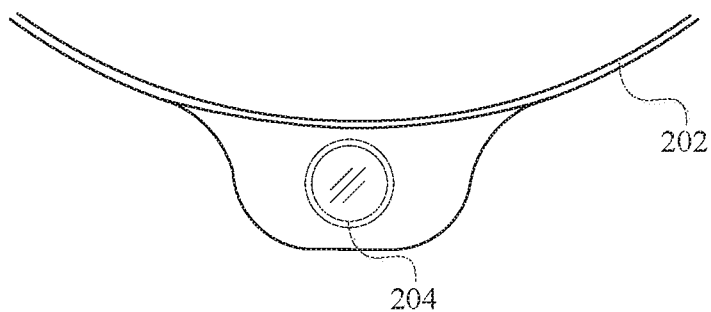
FIGS. 2A-C include a front view, a side view, and a perspective view of a wearable system according to one embodiment.
Figure 2B:
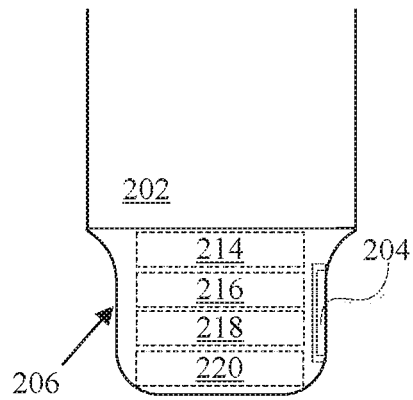
Figure 2C:
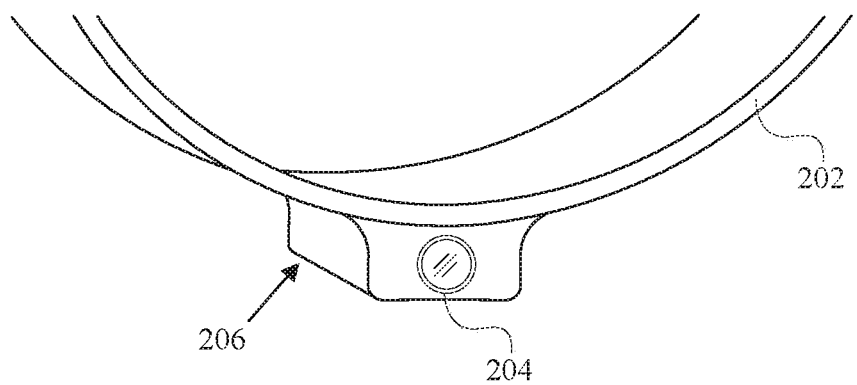

FIGS. 2A-C include a front view, a side view, and a perspective view of a wearable system according to one embodiment. As shown in FIG. 2A, the camera 204 can be coupled to the wristband 202 so that it is positioned and oriented in a particular manner (e.g., displaced from the wristband 202, positioned in the anterior region of the wrist, and oriented to face toward the user's hand). In some embodiments, the camera 204 is integrated into the wristband 202.

The wearable system may also include an electronics compartment 206 that houses some combination of a processor 214, power supply 216, storage medium 218, and communication module 220. More specifically, the electronics compartment 206 can include some or all of the components of computing system 1300 of FIG. 13. The processor 214 can be used to locally process and analyze any recordings, user information, metadata, etc., generated by the camera 204 and other sensors. In some embodiments, a communication module 220 transmits some or all of this information (i.e., the recordings, user information, metadata, etc.) to a remote computing device for processing and analyzing. As will be described below with respect to FIG. 10, the processor 214 could also identify spatial flags in the recordings. A distributed processing system may also be employed in some embodiments. That is, some processing may be done locally (e.g., by processor 214 of the wearable system) and some processing may be done remotely (e.g., by a processor of the remote computing device).

The camera 204 and each of the sensor(s) are coupled to a power supply 216. Examples of a power supply 216 include, but are not limited to, a battery, a replaceable and/or rechargeable battery pack, a solar cell, some other regenerative power source, or any combination thereof. For example, the power supply 216 may be a set of rechargeable lithium ion batteries. The rechargeable batteries may also be adapted to be recharged via a universal serial bus ("USB") connection to a mobile phone, tablet, personal computer (e.g., laptop or desktop), or power outlet converter. The wearable system may also permit alternative connectors such as Apple Lightning or micro USB. The connector may also be used to transmit recordings, user information, metadata, etc., from the wearable system to another device or system. For example, a micro USB to USB adapter may allow the wearable system to transmit the recordings, user information, metadata, etc., to a laptop for further processing and analyzing.

The electronics compartment 206 can also include a storage medium 218 configured to store recordings, user information, metadata, etc., or some combination thereof. In some embodiments, the storage medium 218 is communicatively coupled to a remote storage (e.g., cloud storage or storage of display devices 1204 of FIG. 12) over a network (e.g., Internet, Bluetooth, local area network, wide area network, point-to-point dial-up connection). Recordings may be transmitted to cloud storage, a network-accessible device associated with the user, or another network-accessible device associated with an interested party (e.g., via Short Message Service (SMS), Multimedia Messaging Service (MMS), or email). The storage medium 218 can also be configured to store instructions for one or more of the processes described herein.

The wearable system is able to transmit the recordings, user information, metadata, etc., using a communication module 220 (e.g., a Bluetooth chip or an antenna) that is configured to receive and transmit the information described above. As will be described below with respect to FIG. 12, the communication module 220 can be communicatively coupled to a mobile phone, tablet, laptop, server, etc. For example, the communication module 220 may transmit a portion of a recording to the user's mobile phone for review. As another example, the communication module 220 may transmit the metadata (e.g., time medication was administered, patient unique identifier, medication regimen information) to a server for retrieval by an interested third party.

Figure 3:
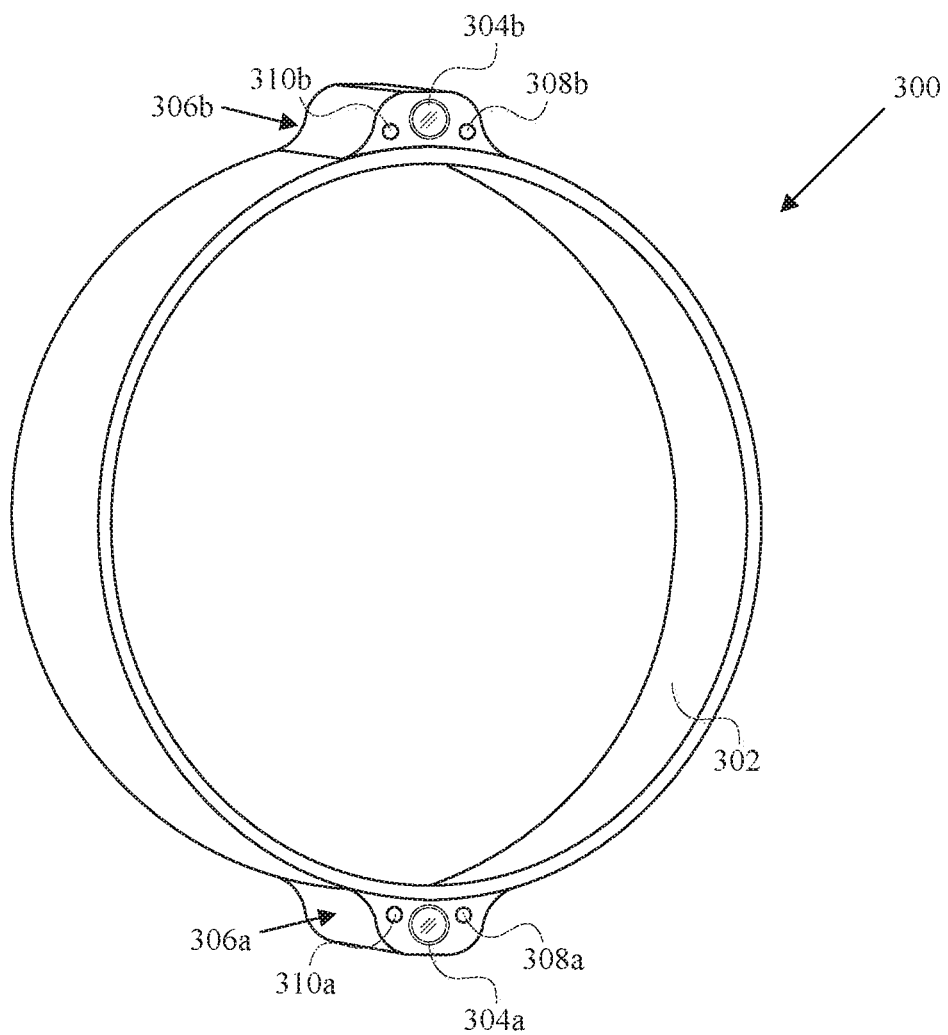
FIG. 3 is a perspective view of a wearable system that includes a wristband, a plurality of cameras, a plurality of electronics compartments, and a plurality of sensors (e.g., electromagnetic sensors and motion sensors).

FIG. 3 is a perspective view of a wearable system 300 that includes a wristband 302, a plurality of cameras 304a-b, a plurality of electronics compartments 306a-b, and a plurality of sensors (e.g., electromagnetic sensors 308a-b, motion sensors 310a-b).

The cameras 304a-b can be used to visually record (e.g., capture still images or video) activities involving the user's hand(s) and/or fingers. As shown in FIG. 3, a plurality of cameras 304a-b that each provide a different view of the user's hand and fingers can be coupled to the wristband 302. The cameras 304a-b may be positioned in particular locations (e.g., anterior and posterior regions of the wrist) in order to achieve an unobstructed view that results in more accurate identification of the actions and/or gestures performed by the user.

The wearable system 300 can also include a plurality of sensors, some of which may perform the same or similar functions. For example, multiple electromagnetic sensors 308a-b may be coupled to the wristband 302 at different positions for more accurate sensing of electromagnetic variations. Similarly, multiple motion or positional sensors 310a-b may be used to more accurately track the position and orientation of the wearable system 300. In some embodiments, more than one electronics compartment 306a-b may be necessary to provide sufficient electrical and/or processing power to the cameras 304a-b, sensors, communication modules, etc. While each electronics compartment 306a-b is depicted as including one of the cameras 304a-b, electromagnetic sensors 308a-b, and motion sensors 310a-b, other configurations could also be implemented. For example, a single electronics compartment positioned lateral to the user's wrist may provide power to components located in both the anterior and posterior regions of the user's wrist. As another example, the wearable system 300 could include multiple cameras 304a-b that are displaced from the wristband 302 and one or more sensors that are integrated into the wristband 302, or vice versa.

Figure 4A:
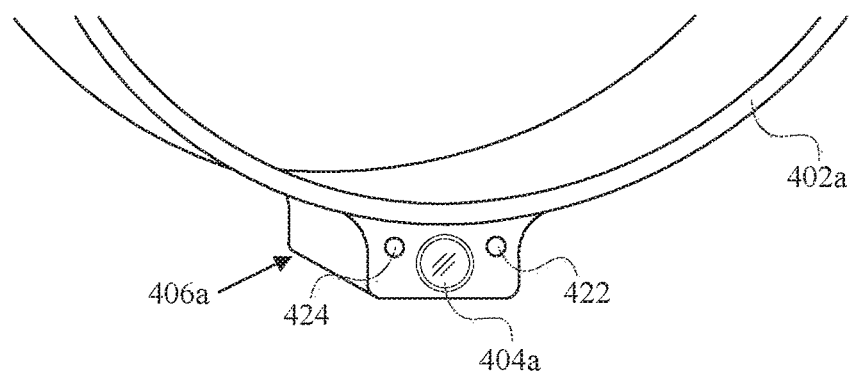
FIGS. 4A-C are perspective views of wearable systems according to various embodiments.
Figure 4B:
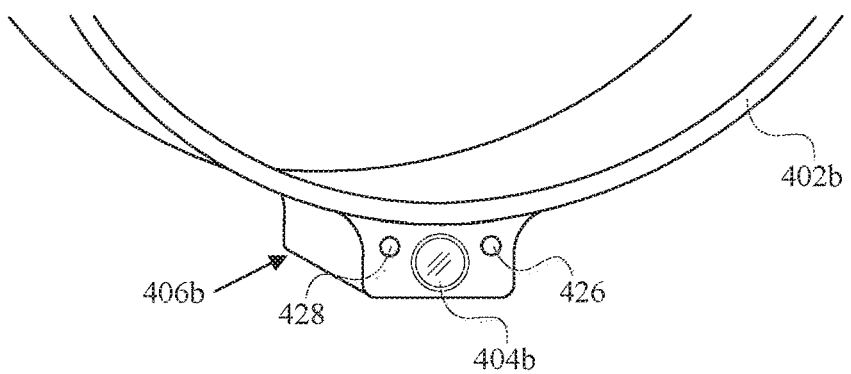
Figure 4C:
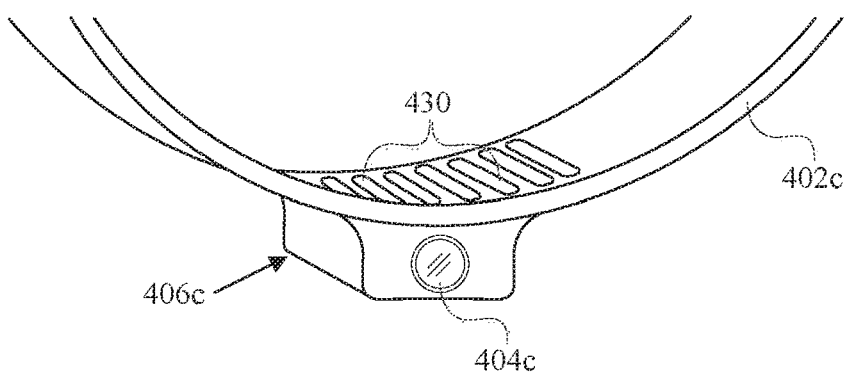

FIGS. 4A-C are perspective views of wearable systems according to various embodiments. Each wearable system may include a wristband 402a-c, a camera 404a-c, an electronics compartment 406a-c, and some combination of sensors. For example, a wearable system could include a sound sensor 422 (e.g., a microphone), climate sensor 428, pressure sensor 430, or an RFID sensor.

The sound sensor 422 may detect variations in ambient sound and identify particular sounds. Examples of particular sounds include a vocal command (e.g., "turn on" or "begin recording"), the opening of a blister pack of medication, or a depression of an inhaler. The climate sensor 428 may monitor ambient climate conditions, such as the ultraviolet index, humidity, temperature, atmospheric pressure, illuminance level, etc. In some embodiments, one or more pressure sensors 430 are embedded within the wristband 402c on the side of the wristband nearer the user's wrist (i.e., inside an interior region defined by the wristband 402c). When the pressure sensors 430 are located in the anterior region of the user's wrist, the pressure sensors 430 can detect contractions in the tendons and changes in tendon tension. The contractions and changes in tension may be used to control various aspects of the wearable system or to identify particular actions, such as grasping and releasing.

Some embodiments also include a speaker 424 and/or an image projector 426. The speaker 424 can be configured to audibly relay a reminder, a notification, or an instruction to the user. The audible reminder may prompt the user to administer medication. As another example, an instruction may be presented to the user by a third party (e.g., a physician, nurse, or pharmacist) regarding proper administration of the medication or execution or a healthcare activity, such as using an epinephrine autoinjector or an insulin pen. One skilled in the art will recognize that reminders may also be visual or tactile in nature. For example, the wearable system may alert the user using a visual reminder, which is conveyed by an electronic display or by one or more light emitting diodes (LEDs), or a tactile reminder, which is conveyed by an actuator vibrating or pulsing. In some embodiments, an image projector 426 is oriented so that it can project an image onto the user's hand or onto another surface (e.g., a table or wall). The image may include information about the user, medication, or medication/healthcare regimen, a notification, an instruction, etc.

One skilled in the art will recognize that a particular combination of sensors may be desirable in certain instances. For example, a wearable system may include a speaker 424 and a sound sensor 422 that permit a user and a third party to communicate with one another regarding a medication, a medication regimen, administration of the medication, etc. As another example, a wearable system may include a speaker 424 and an image projector 426 that allow the third party to convey instructions both visually and audibly.

Figure 5A:
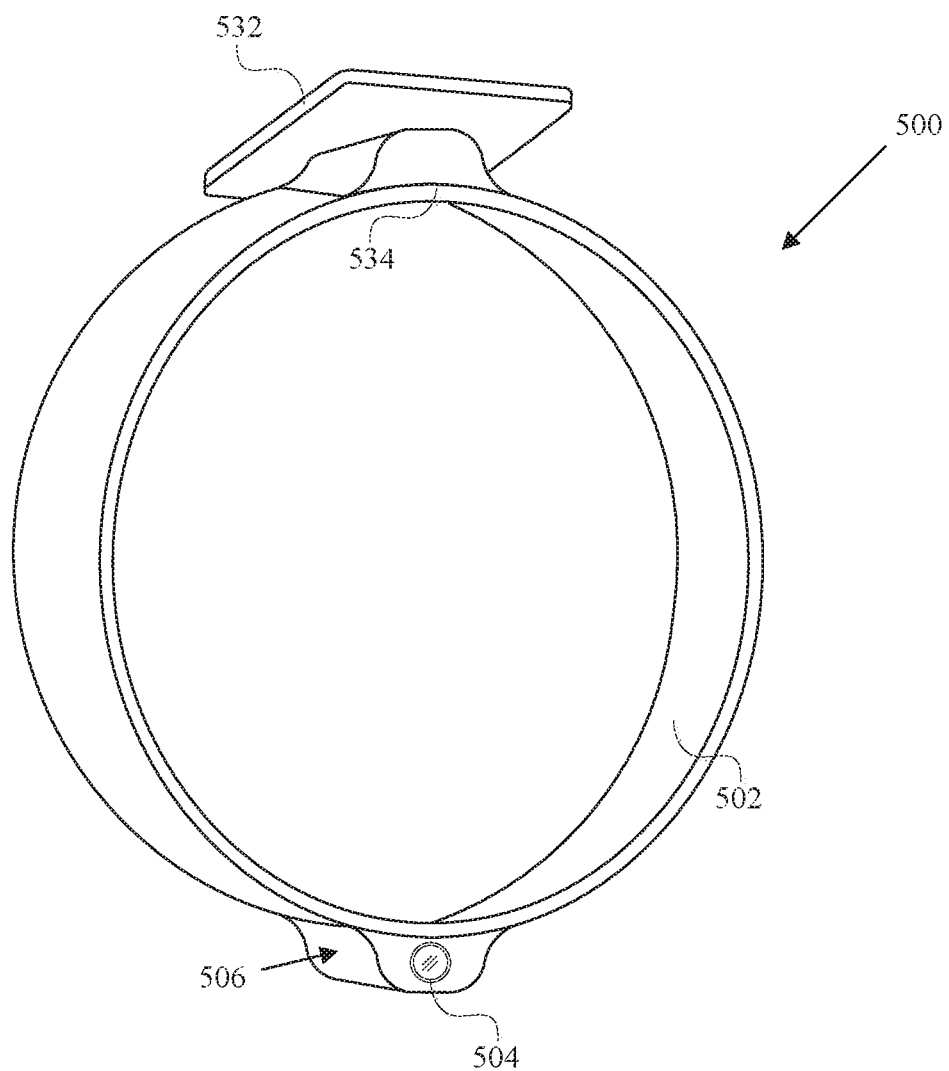
FIGS. 5A-B are perspective views of a wearable system that includes an electronic display.
Figure 5B:
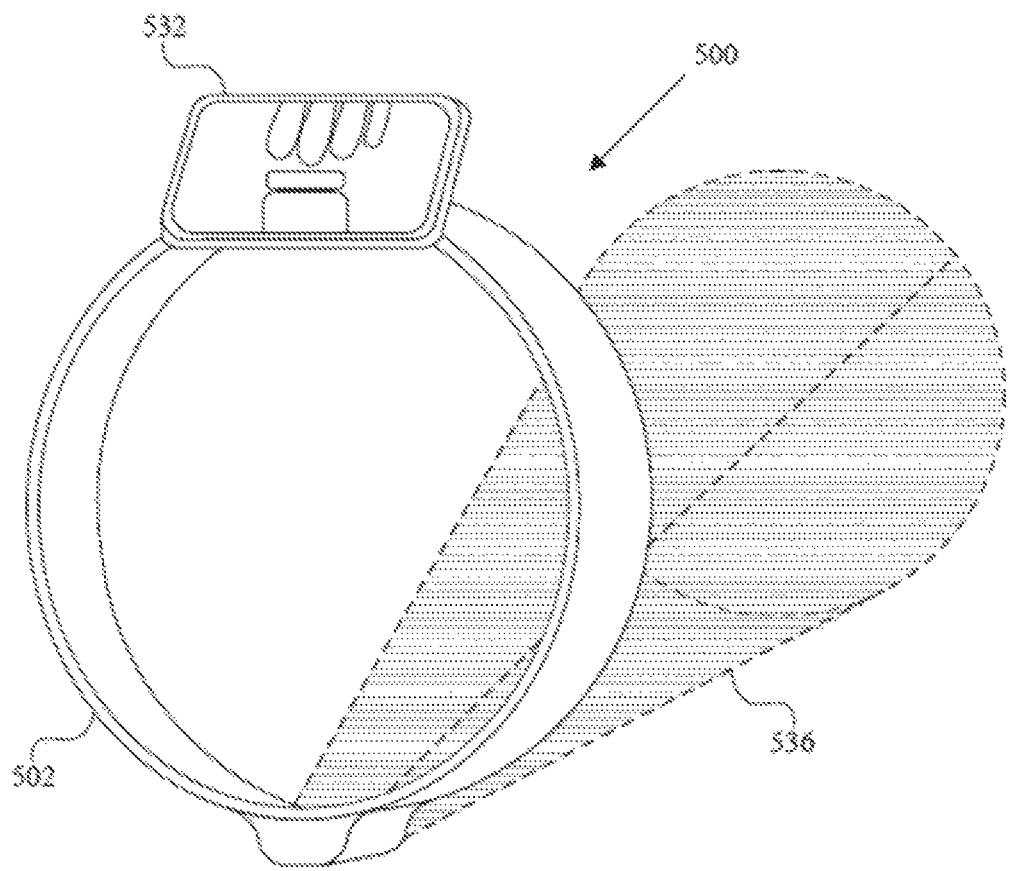

FIGS. 5A-B are perspective views of a wearable system 500 that includes an electronic display 532. More specifically, in some embodiments the wearable system 500 includes a camera 504 and an electronic display 532 that is coupled to a wristband 502 via a mount 534. As further described below with respect to FIGS. 6A-B, the mount 534 may permit the electronic display 532 to be viewed at different angles and orientations.

The camera 504 can be used to generate a recording of an activity involving the user's hand(s), fingers, or both. In some embodiments, the recording is analyzed to determine what activity (e.g., gesture or position) caused the recording to be generated. For example, a camera 504 can generate a visual recording (e.g., still image or video) upon sensing a particular gesture and/or determining the wearable system 500 is in proximity to a bottle of medication, both of which typically indicate that medication is likely to be promptly administered by the user. The gesture may be a particular hand or finger position, movement, or combination of positions and movements.

As shown in FIG. 5B, the camera 504 can be located in an anterior region of the wrist and oriented toward the user's hand. In such embodiments, the camera 504 generates a viewing field 536 that includes at least part of the user's hand and any objects the user interacts with using the hand or fingers. The recordings can be presented to the user on the electronic display 532. Here, for example, the electronic display 532 shows the user's fingers reaching toward a bottle of medication. The electronic display 532 can also be used to display information about a medication or a regimen, present adherence reports, and visually relay reminders, notifications, and instructions. For example, a third party (e.g., a physician, nurse, pharmacist, or insurance representative) may remotely provide guidance to a user for administering a medication, selecting an appropriate medication (e.g., one that is covered by insurance), taking a blood pressure measurement, etc.

Figure 6A:
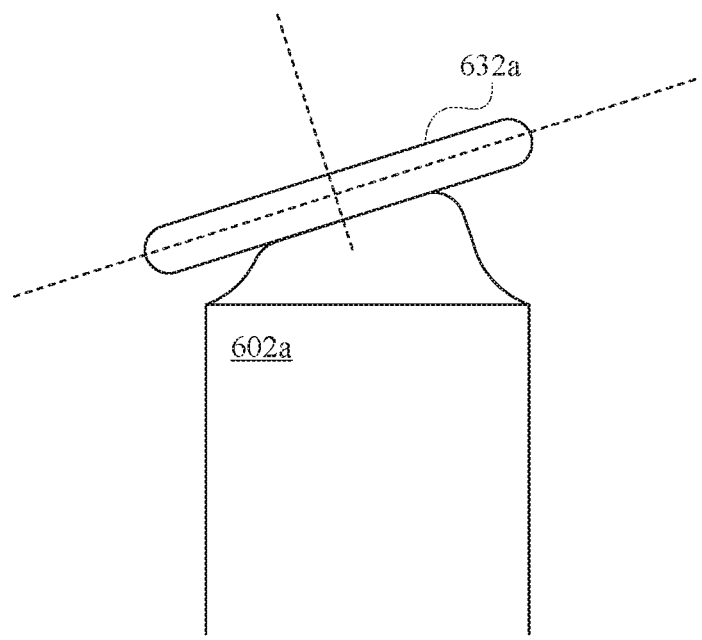
FIGS. 6A-B are side views of electronic displays that are attached to a wristb by mounts according to some embodiments.
Figure 6B:
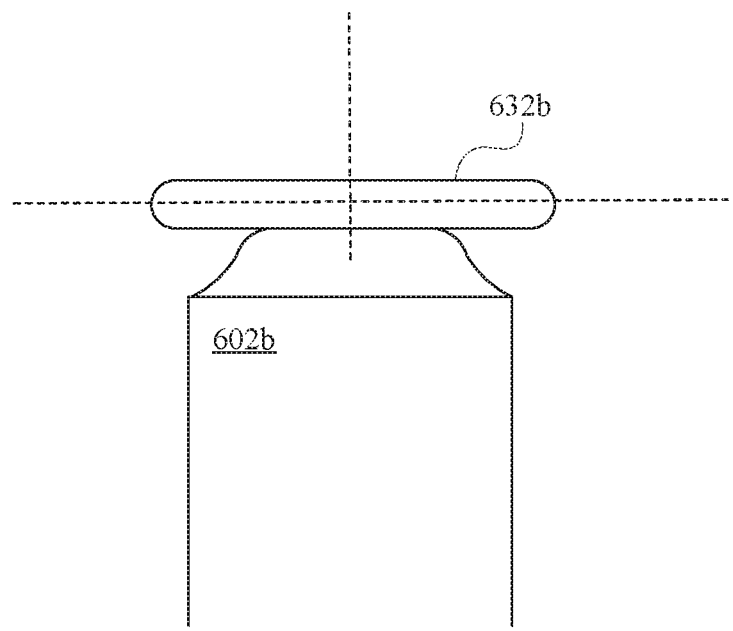

FIGS. 6A-B are side views of electronic displays 632a-b that are attached to a wristband 602a-b by mounts 634a-b according to some embodiments. The mounts 634a-b can be used to change the position and/or orientation of the electronic displays 632a-b. For example, in some embodiments the mount 634a orients the electronic display 632a at a particular angle, as illustrated in FIG. 6A. In other embodiments, the mount 634b simply connects the electronic display 632b to the wristband 602b, as illustrated in FIG. 6B. The electronic display 632a-b could also be integrated into the wristband 602a-b itself, thereby rendering a mount 634a-b unnecessary as the electronic display 632a-b typically does not extend above the surface of the wristband 602a-b in such embodiments.

The mount 643a-b can also provide the user additional flexibility with respect to how the electronic display 632a-b is viewed. For example, the mount 634a-b may permit the electronic display 632a-b to swivel, tilt, or pivot and be viewed at different orientations. The mount 634a-b could also be detachable from the wristband 602a-b. Such a feature may be particularly desirable if the electronic display 632a-b includes, or is communicatively coupled to, a storage that maintains recordings, adherence reports, user information, etc. In some embodiments, the electronic display 632a-b is connectable to another computing device (e.g., a mobile phone, tablet, or laptop) via a connector (e.g., a USB, Apple Lightning, or micro USB cable) that allows information to be transferred to, and received from, the storage. The wearable system can also be configured to transmit and receive information wirelessly over a network (e.g., the Internet, Bluetooth, or a local area network). Various embodiments may support either or both of these capabilities.

Figure 7A:
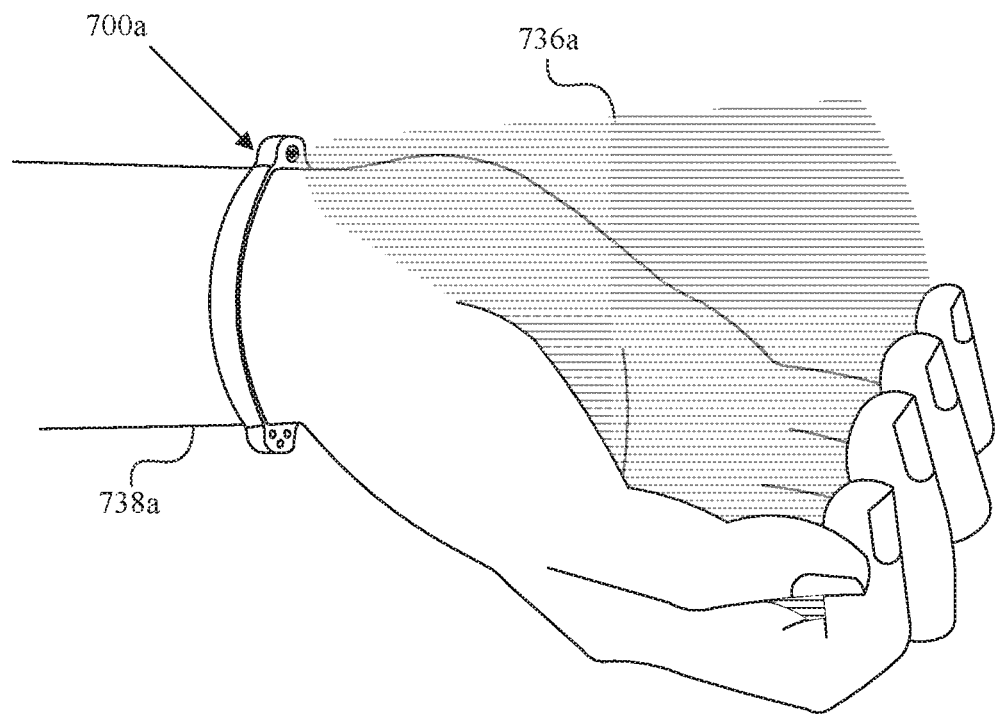
FIG. 7A depicts a viewing field projected by a camera of a wearable system according to some embodiments.

FIG. 7A depicts a viewing field 736a that is projected by a camera 704a of a wearable system 700a. The wearable system 700a is worn around the wrist of a user 738a. The wearable system 700a is typically worn so the camera 704a is oriented toward the user's hand. More specifically, the camera 704a can be positioned so the corresponding viewing field 736a includes the user's hand and fingers. The camera 704a can be configured to generate a visual recording of certain activities. In some embodiments, the camera 704a or another sensor (e.g., a depth sensor or image sensor) begins recording in response to detecting a particular gesture or motion, such as bringing the hand toward the user's face, crossing arms, or shaking hands. The gesture(s) may be used to activate the camera 704a or may serve as command inputs (e.g., to begin recording or transmit past recordings to another processing system). The wearable system 700a may include a storage and a processor configured to analyze the recordings and construct new algorithms or improve existing algorithms for detecting gestures.

Figure 7B:
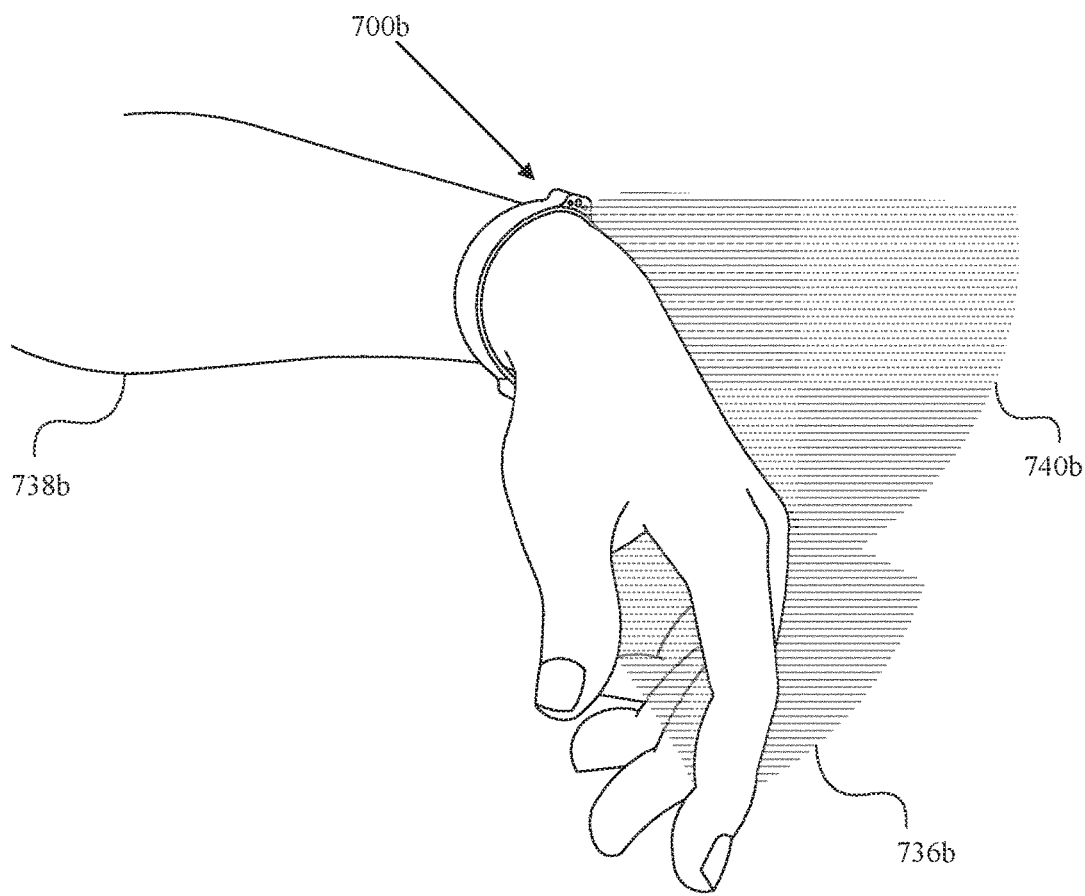
FIG. 7B depicts multiple viewing fields projected by multiple cameras of a wearable system according to some embodiments.

FIG. 7B depicts multiple viewing fields 736b, 740b projected by multiple cameras of a wearable system 700b according to some embodiments. The distinct cameras provide different viewpoints of the user's hand and fingers as illustrated by the viewing fields 736b, 740b. The wearable system may be configured to activate one or more of the cameras 702b, 704b based on the content of one or both viewing fields 736b, 740b.

In some instances, the user 738b may wear a wearable system (e.g., wearable systems 700a and 700b) on each wrist. Such a configuration can be used to generate stereo images (i.e., offset two-dimensional images) or three-dimensional recordings, spatial information, etc. Multiple wearable systems could be used to more accurately track the user's arm movement and activities, particularly if the activities involve both of the user's hands working together. Additional spatial information can also be generated when the user 738b wears wearable systems on both wrists. For example, inertial sensors or positional sensors coupled to each of the wristbands can be used to generate three-dimensional spatial information. The spatial information may be used to generate a three-dimensional model of the user's hand and/or finger movement and gestures in three-dimensional space.

Figure 7C:
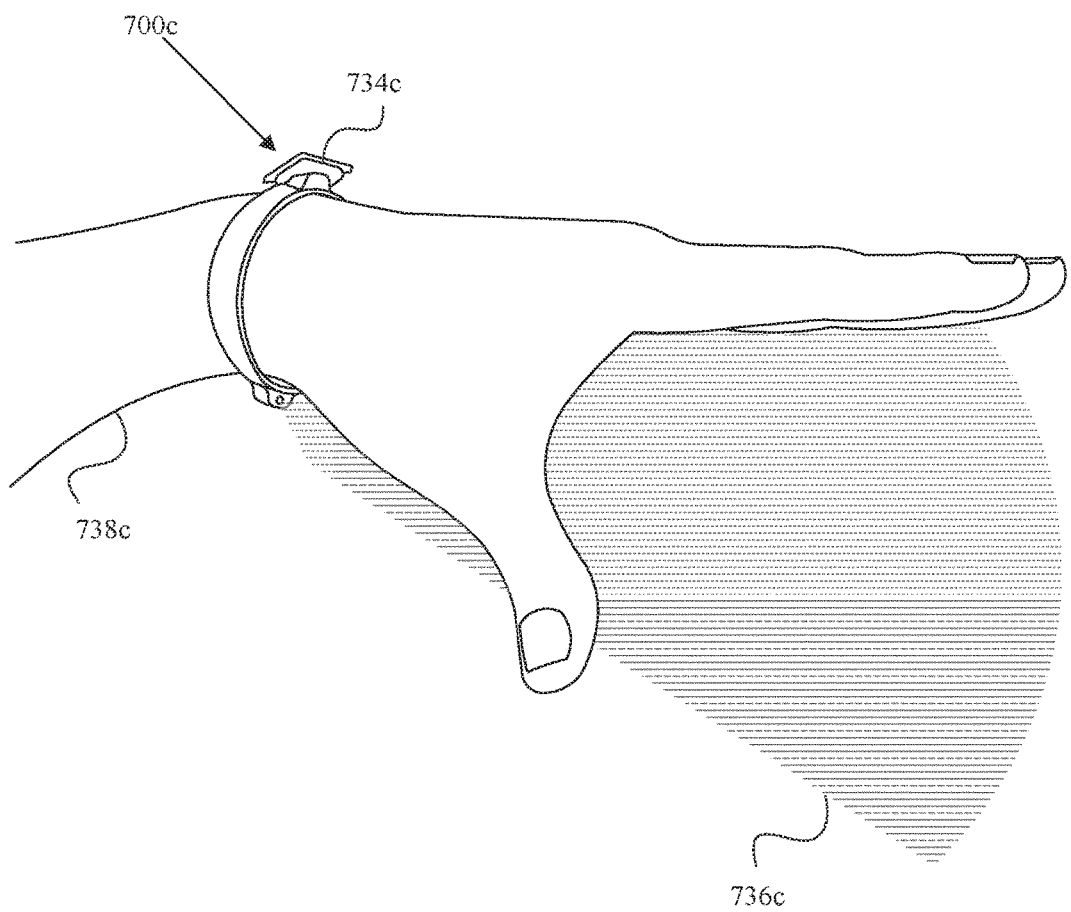
FIG. 7C depicts a viewing field projected by a camera of a wearable system according to some embodiments.

FIG. 7C depicts a viewing field 736c projected by a camera of a wearable system 700c according to some embodiments. The wearable system 700c can include an electronic display 734c that presents at least a portion of what is within the viewing field 736c. In some embodiments, visual recordings captured by the camera are transmitted to and presented to the user 738c by the electronic display 734c in real-time. The electronic display 734c can also be used to view past recordings, adherence reports, reminders, user information, recording settings, etc.

Figure 7D:
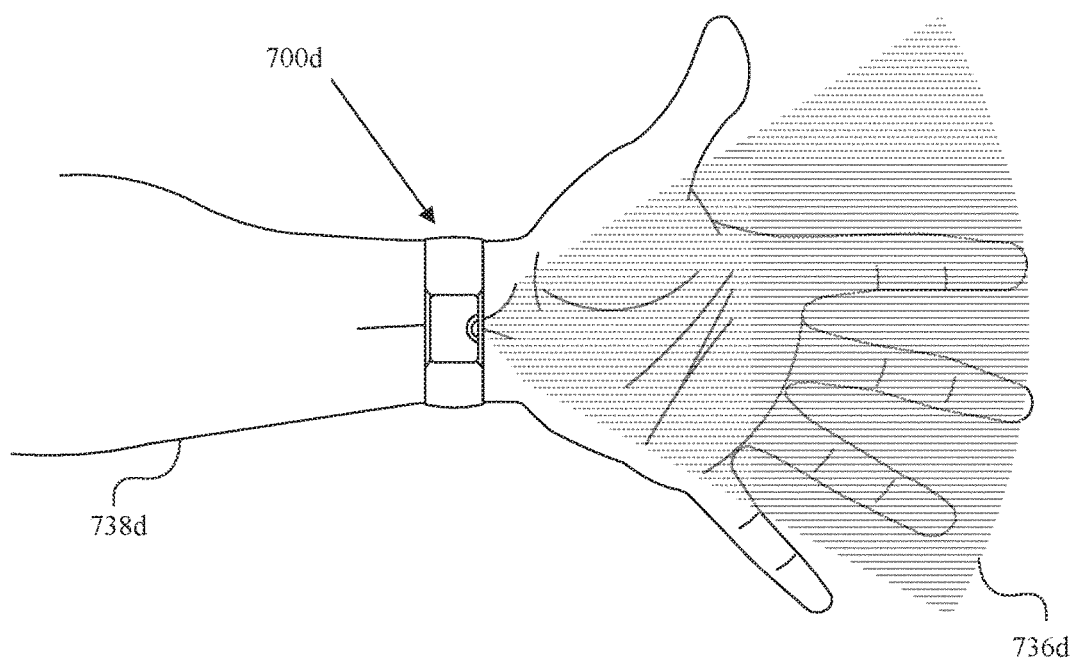
FIG. 7D depicts an anterior view of a viewing field projected by a camera of a wearable system according to some embodiments.

FIG. 7D depicts an anterior view of a viewing field 736d projected by a camera of a wearable system 700d. In some embodiments, the viewing field 736d is adjustable to limit the angle, width, depth, etc., of viewing. The user 738d may be able to modify these viewing settings using an electronic display that is coupled to the wearable system 700d or an application that is running on a computing device that is communicatively coupled to the wearable device 700d. Additionally or alternatively, the wearable system 700d may come equipped with a particular camera selected for a particular application (e.g., close-range viewing or high resolution recordings).

Figure 8:
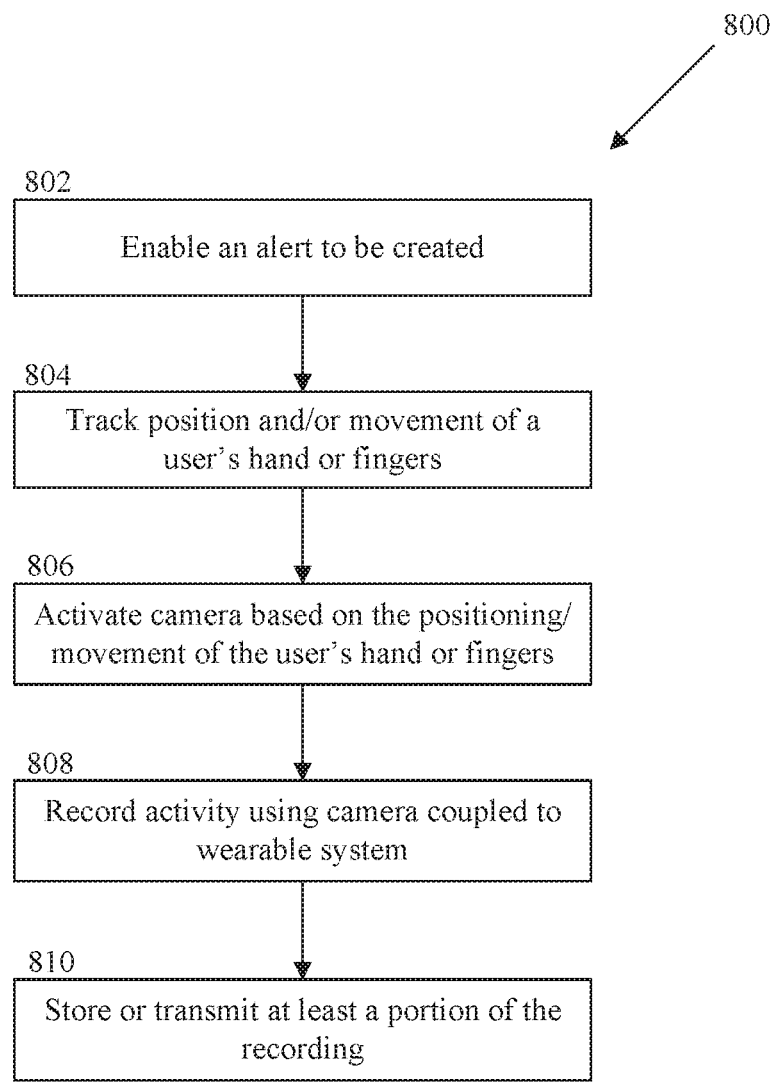
FIG. 8 is a block diagram of a process for monitoring adherence to a medication regimen or a healthcare regimen according to various embodiments.

FIG. 8 is a block diagram of a process 800 for monitoring adherence to a medication regimen or a healthcare regimen. At block 802, the wearable system can initially allow the user, an administrator (e.g., a manufacturer of the wearable system), or an interested third party (e.g., a family member or physician) to create an notification. The notification may correspond to activity that is required as part of a medication or healthcare regimen.

At block 804, a wearable system tracks the position or movement of a user's hand and/or fingers. Position and/or movement can be determined using a camera, a depth sensor, an image sensor, etc. At block 806, the wearable system activates a camera based on the positioning and/or movement of the user's hand and/or fingers. Said another way, the camera is activated in response to the wearable system determining the user is likely to perform an act (e.g., administer medication) in compliance with the medication or healthcare regimen. For example, the camera may be activated when the wearable system identifies a prerecorded activity corresponding to the user. The user may have personalized spatial motions or gestures, such as lifting a coffee mug, recording a signature, opening a container of medication, etc., that distinguish the user from other users. Activation of the camera may also be based on the duration of a particular gesture or movement (e.g., waiving a hand or raising an arm for a predetermined period of time).

At block 808, the wearable system uses the camera to record an activity associated with the medication or healthcare regimen. For example, the recording may be of the user administering medication in accordance with a medication regimen. As another example, the recording may be of the user partaking in an activity (e.g., measuring blood pressure) in accordance with a healthcare regimen. The wearable system can differentiate various activities, such as walking and eating, by analyzing the recordings and using information extracted from previous recordings. At block 810, the wearable system stores at least a portion of the recording in a storage or transmits at least a portion of the recording to another computing device. Some wearable systems may be configured to archive some recordings locally and also transmit recordings across a network to a mobile phone, tablet, laptop, etc. In some instances it may be desirable for the wearable system to store or transmit the entire recording to the other computing device, while in other instances the wearable system may only store or transmit a portion of the recording. For example, an interested third party may only want a fragment of a recording that shows a user measuring blood pressure in order to determine whether the measurement was completed.

Figure 9:
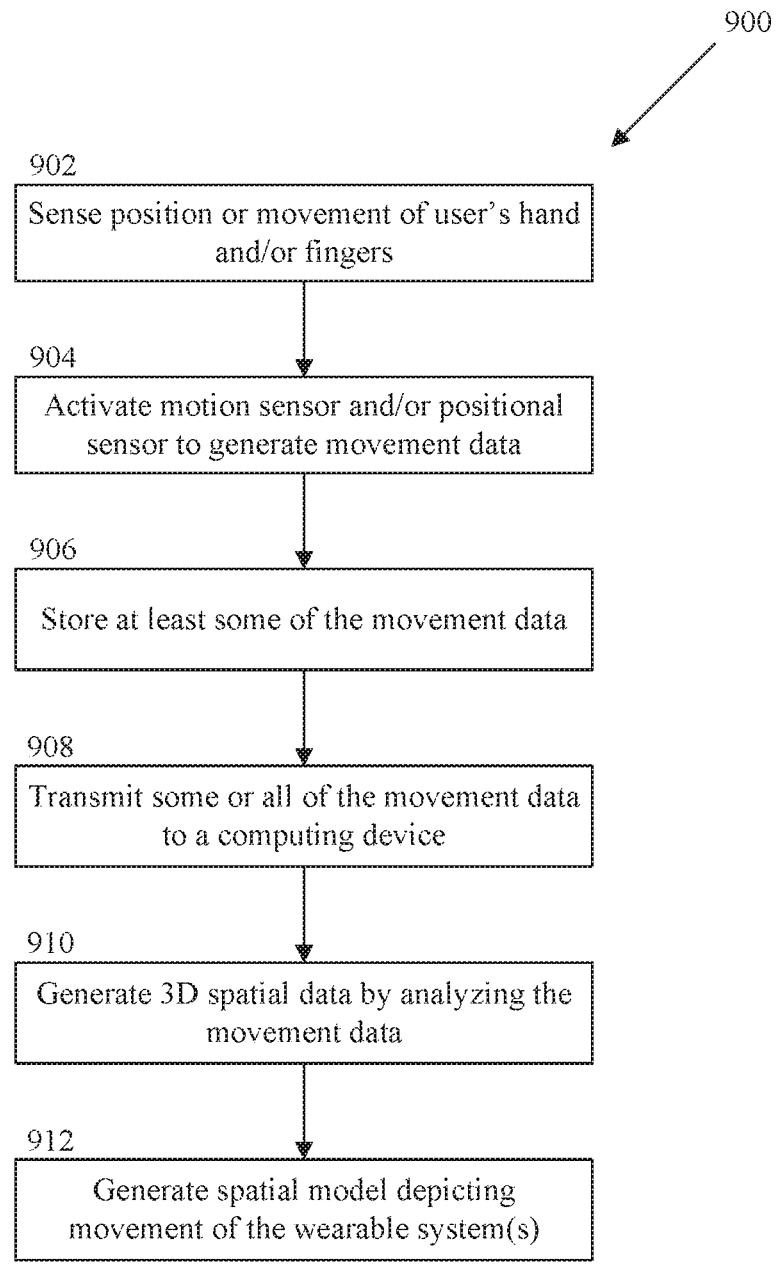
FIG. 9 is a block diagram of a process for generating a three-dimensional spatial model using data generated by wearable system.

FIG. 9 is a block diagram of a process 900 for generating a three-dimensional spatial model using data generated by wearable system. At block 902, the wearable system monitors the position or movement of a user's hand and/or fingers. As described above, the wearable system may be configured to identify particular (e.g., prerecorded) movements or gestures that correspond to the user. At block 904, the wearable system activates a motion sensor and/or a positional sensor that generate(s) movement data. The motion sensor and/or positional sensor may be activated in response to determining the wearable system is in proximity to a particular item (e.g., a bottle of medication), the user has performed a particular action (e.g., provided a vocal command to begin tracking movement), etc.

At block 906, the wearable system stores at least some of the movement data in a local memory. At block 908, the wearable system transmits (e.g., via an antenna or a communication module) some or all of the movement data to a computing device. Examples of a computing device include mobile phones, tablets, personal computers (e.g., laptops), and servers. The computing device may be operated by the user or an interested third party (e.g., a physician, nurse, or family member).

At block 910, the wearable system or the computing device can generate three-dimensional spatial data by analyzing the movement data. The movement data may need to be processed in order to determine how different types of data generated by different types of sensors are related. For example, the movement data could be generated by a positional sensor, an inertial sensor, an RFID proximity sensor, etc. Moreover, if the user equips a wearable system on each arm, the movement data corresponding to each arm must be harmonized. At block 912, the wearable system or the computing device can generate a three-dimensional spatial model using the spatial data. The spatial model can depict the movement of the wearable system(s) in a three-dimensional space. The spatial model may be used to improve the movement, position, and gesture recognition capabilities of the wearable system.

Figure 10:
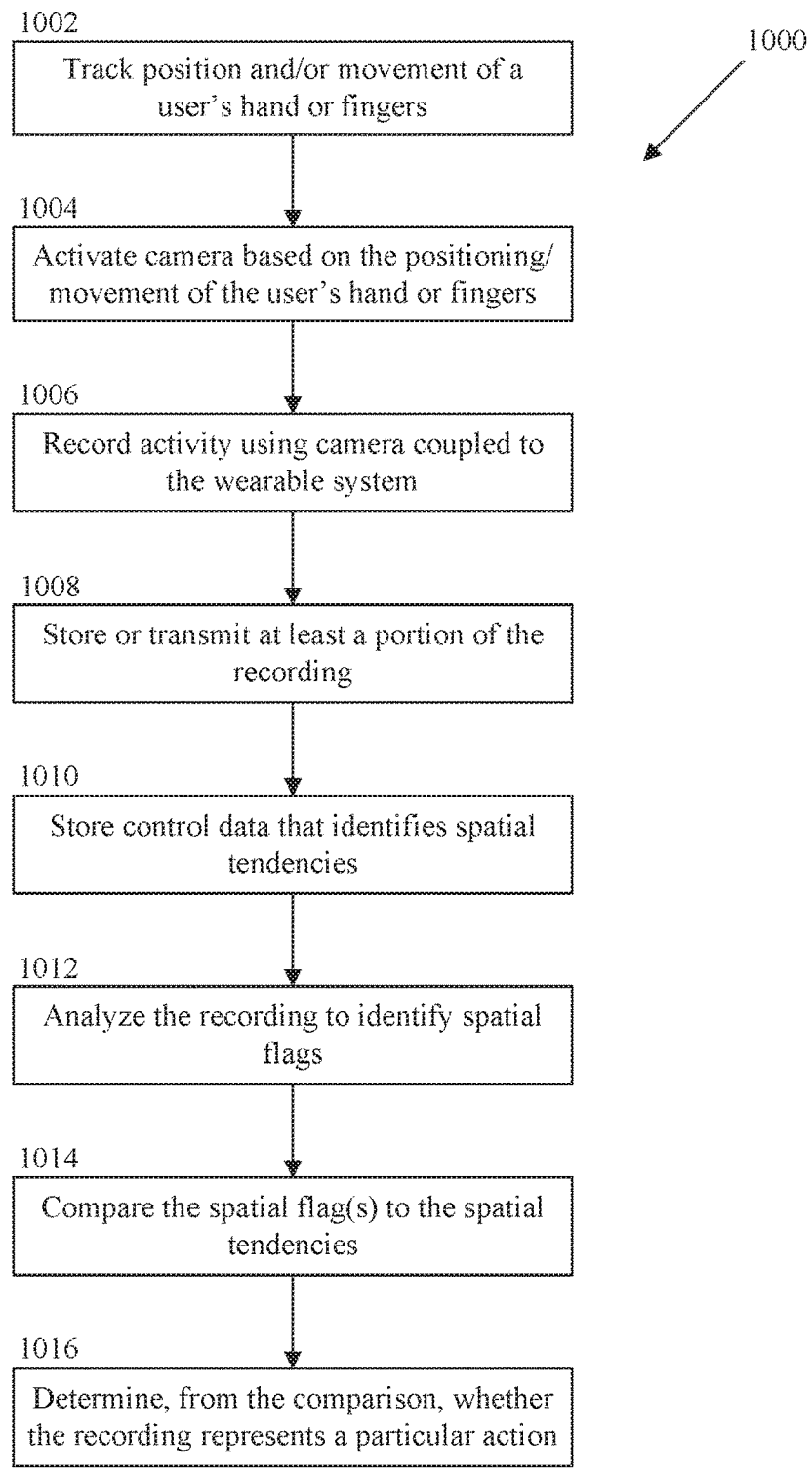
FIG. 10 is a block diagram of a process for processing and identifying spatial flags associated with a particular user according to some embodiments.

FIG. 10 is a block diagram of a process 1000 for processing and identifying spatial flags associated with a user.

Blocks 1002, 1004, 1006, and 1008 may be substantially similar to blocks 804, 806, 808, and 810, respectively.

At block 1010, the wearable system can store control data that identifies one or more spatial tendencies associated with the user. The control data may be provided by another entity (e.g., an administrator who manufactured the wearable device or a healthcare professional) or generated by the wearable system based on prior recordings. Each spatial tendency represents a particular movement or gesture that the wearable system can be trained to recognize. For example, a spatial tendency may include information describing the manner in which the user grabs and opens a bottle of medicine or operates a blood pressure monitor. The control data can be stored locally by the wearable system or remotely in a storage that is accessible to the wearable system. At block 1012, the wearable system analyzes the recording to identify whether any spatial flags are present. A spatial flag is a unique movement, position, gesture, etc., that can be identified in the recording.

At block 1014, the wearable system compares the spatial flags found within the recording to the known spatial tendencies of the user. At block 1016, the wearable system can determine whether the recording has captured the user performing a particular action based on the comparison. More specifically, the wearable system may be able to determine which action(s) have been performed by mapping the spatial flag(s) to a stored activity record (i.e., a spatial tendency) associated with the user. If a positive determination is made, the wearable system can confirm the corresponding action was performed.

Figure 11:
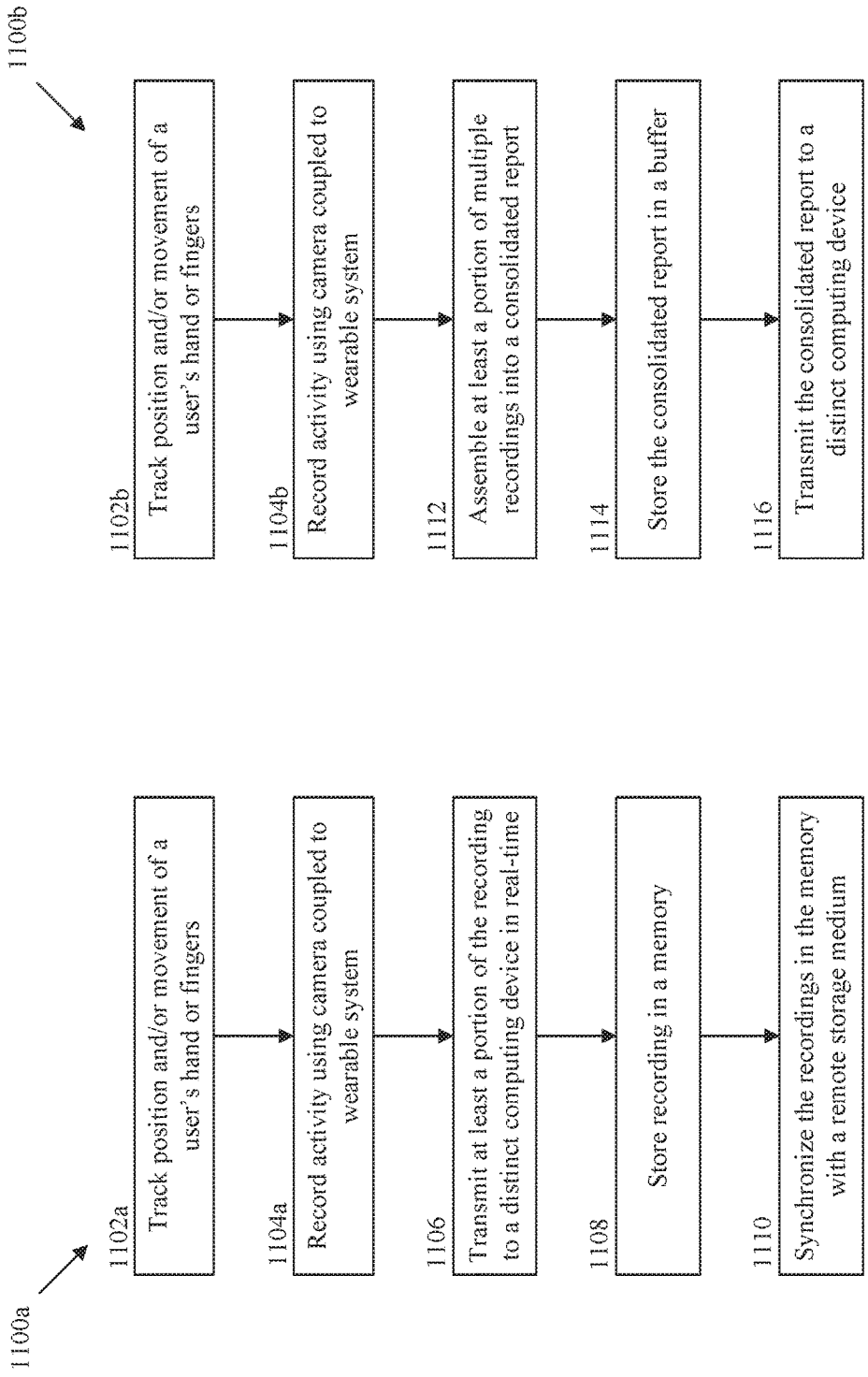
FIGS. 11A-B are block diagrams of different processes for storing recordings.

FIGS. 11A-B are block diagrams of different processes 1100a-b for storing recordings. At blocks 1102a-b, the wearable system tracks the position and/or movement of the user's hand or fingers. For example, the wearable system may monitor whether the user performs specific gestures. At blocks 1104a-b, the wearable system records the activity using a camera that is coupled to the wearable system and stores the recording in a storage (e.g., a storage or buffer).

In some embodiments, the recording is transmitted to a distinct computing device (e.g., mobile phone, tablet, laptop, server) in real-time. For example, at block 1106 the wearable system transmits at least a portion of the recording in real-time to the distinct computing device across a network. At block 1108, the wearable system, the distinct computing device, or both can then store the recording in a memory. In some embodiments, the wearable system is configured to synchronize the recordings in the local memory with those in a remote storage medium, as shown in block 1110. The remote storage medium may be associated with the distinct computing device or may be distinct from both the wearable system and the distinct computing device. For example, the remote storage medium may represent cloud storage or a personal backup server. One skilled in the art will recognize the wearable system and remote storage medium may be configured to synchronize at particular times, upon command, when a particular number or type of recordings are generated, etc.

In some embodiments, recordings are temporarily stored on the wearable system and then transmitted to the distinct computing device together in a consolidated report. For example, at block 1112 the wearable system can assemble at least a portion of multiple recordings into a consolidated report. The consolidated report may also include other information, such as user information (e.g., a unique identifier or medication regimen details), metadata (e.g., specifying the number of recordings, flagged actions, or timestamps), and other media (e.g., audio files). At block 1114, the wearable system can stores the consolidated report in a memory (e.g., a buffer). At block 1116, the wearable system subsequently transmits the consolidated report to the distinct computer device for processing, analyzing, viewing, etc. In some embodiments the recordings are removed from the memory once transmitted to the distinct computing device in the consolidated report, while in other embodiments the wearable system retains some or all of the recordings transmitted in the consolidated report within the memory.

It is envisioned that the processes and steps described above may be performed in any sequence and/or in any combination, unless contrary to physical possibility. Moreover, the processes described herein (e.g., processes 800, 900, 1000, 1100a-b) can be continuous in nature, unless otherwise indicated. That is, once the process completed, the process can begin again. For example, a wearable system can continuously track the position and movement of the user's hands and fingers, record activities, generate three-dimensional spatial data based on position of the wearable system, and update a spatial model representing movement of the wearable system in accordance with process 900 of FIG. 9.

Figure 12:
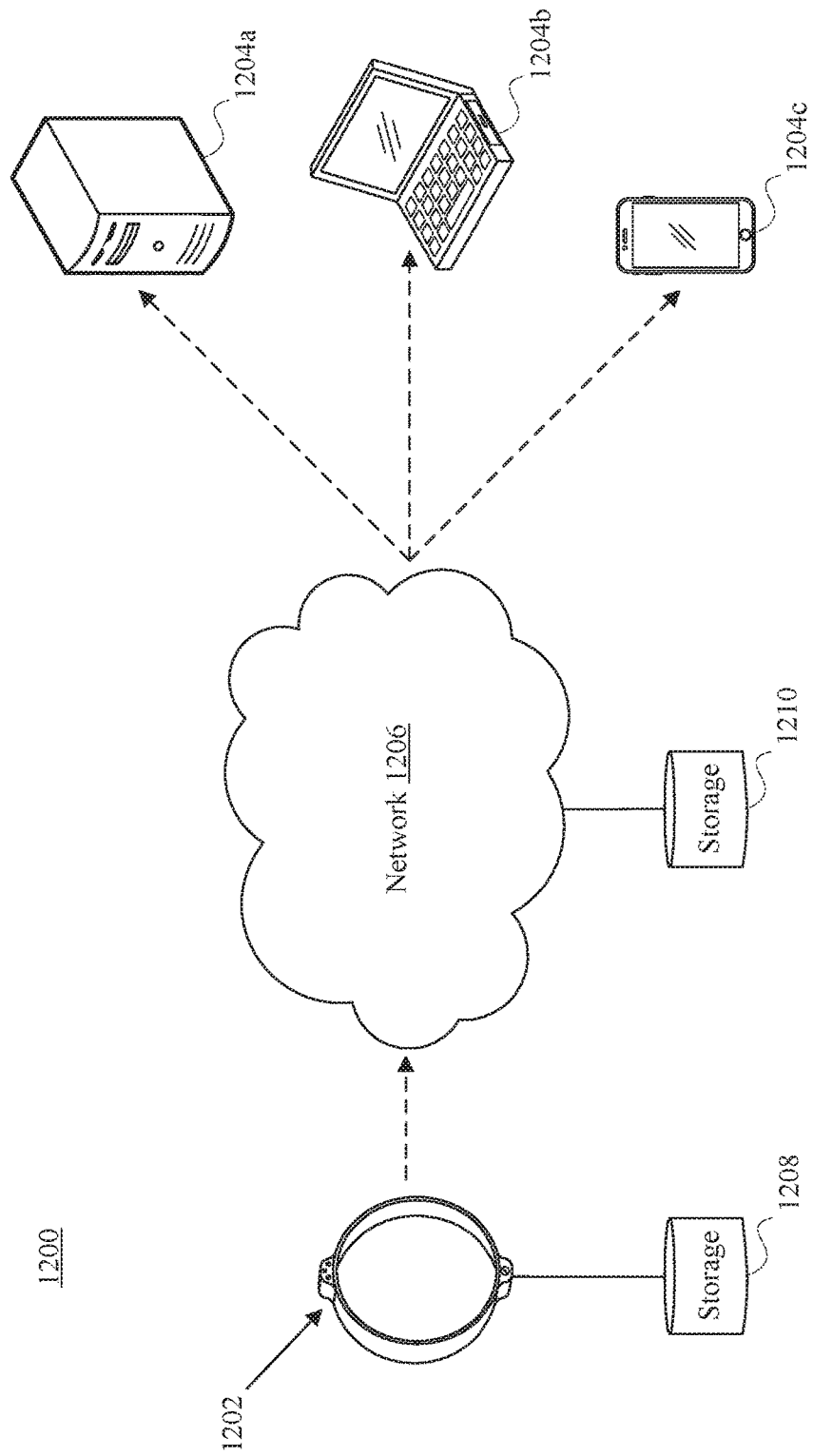
FIG. 12 is a diagram of an exemplary communication network according to some embodiments.

FIG. 12 is a diagram of an exemplary communication network 1200 according to some embodiments. Components of the wearable system 1202 (e.g., sensors, camera, speaker) can be communicatively coupled to one or more electronic devices 1204a-c. The electronic devices 1204a-c can be a mobile phone, tablet, server, etc., that allow a user or a third party (e.g., a physician, drug trial clinician/researcher, or family member) to transmit information to and receive information from the wearable system. For example, a physician may be able to view recordings captured by the wearable system 1202 and thereby monitor the user's adherence to a medication or healthcare regimen. Similarly, a family member could be allowed to view information regarding administration of a medication by the user. The recordings, user information, and administration data may be stored locally on the wearable system 1202 (e.g., within storage medium 1208), remotely in a network (e.g., cloud) storage 1210, or on one or more of the electronic devices 1204a-c. In some embodiments, a distributed storage network utilizes more than one storage medium (e.g., user information may be stored on within storage medium 1208, while recordings are stored in the cloud or network-based storage 1210).

The electronic devices 1204a-c can be coupled, wired or wirelessly, to the wearable system 1202. In some embodiments, the wearable system 1200 is communicatively coupled to one or more electronic devices 1204a-c via a computer system (e.g., computing system 1300 of FIG. 13) that includes an antenna, wireless communication module, etc. The wearable system 1202 can communicate with the electronic devices 1204a-c over a network 1206, such as the Internet, a Bluetooth connection, a local area network, a wide area network, or a point-to-point dial-up connection.

Figure 13:
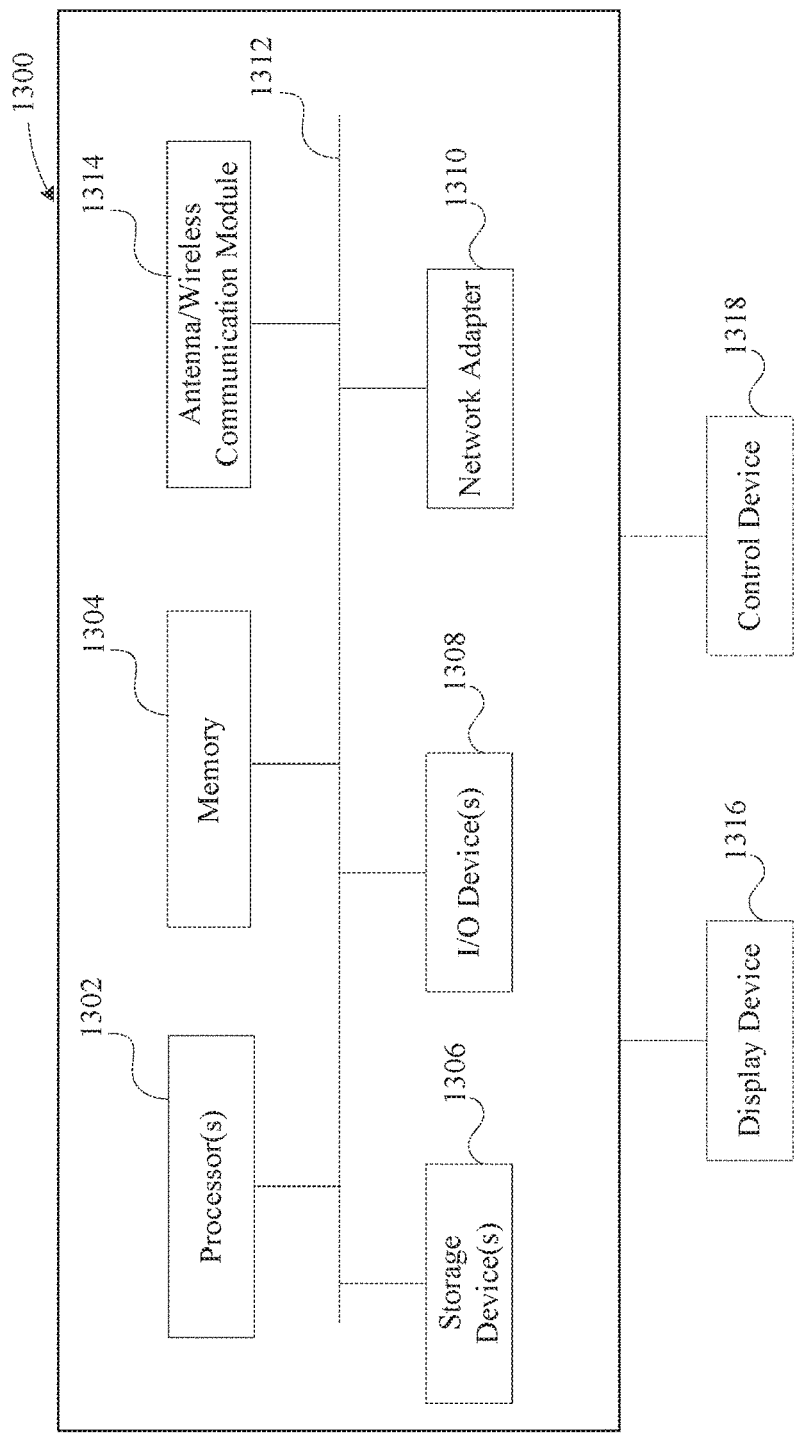
FIG. 13 is a block diagram with exemplary components of a computing system for monitoring adherence to a medication regimen.

FIG. 13 is a block diagram with exemplary components of a computing system 1300 in which at least some of the operations described herein can be implemented. The computing system 1300 may include one or more central processing units ("processors") 1302, a memory 1304, input/output devices 1308 (e.g., keyboard and pointing devices, display devices), storage devices 1306 (e.g., disk drives), network adapters 1310 (e.g., network interfaces), and antennas 1314 that are connected to an interconnect 1612. The interconnect 1312 is illustrated as an abstraction that represents any one or more separate physical buses, point to point connections, or both connected by appropriate bridges, adapters, or controllers. The interconnect 1312, therefore, can include, for example, a system bus, a Peripheral Component Interconnect (PCI) bus or PCI-Express bus, a Hyper-Transport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire."

The memory 1304 and storage devices 1306 are computer-readable storage media that may store instructions that implement at least portions of the described systems and methods. In addition, the data structures and message structures may be stored or transmitted via a data transmission medium, such as a signal on a communications link. Various communications links may be used, such as the Internet, a local area network, a wide area network, a point-to-point dial-up connection, etc. Thus, computer-readable media can include computer-readable storage media (e.g., "non-transitory" media) and computer-readable transmission media.

The instructions stored in memory 1304 can be implemented as software and/or firmware to program the processor(s) 1302 to carry out actions described above. In some embodiments, the software or firmware may be initially provided to the computer system 1300 by downloading it from a remote system through the computing device 1300 (e.g., via network adapter 1310, via antenna 1314). In some embodiments, the antenna 1314 allows information to be sent to, and received from, a display device 1316, a control device 1318, or both. In many instances, the information stored in the memory 1304 may be stored in one of the storage devices 1306, and vice versa. The antenna 1314 can transmit and receive information wirelessly and, accordingly, may also be referred to as a wireless communication module. The display devices 1316 can be, for example, electronic display 532 of FIGS. 5A-B or any of the electronic devices 1204a-c of FIG. 12. The control device 1318 can be a distinct physical device, an application adapted for a wearable system (e.g., configured to be displayed on electronic display 532 of FIGS. 5A-B), a mobile application adapted for a mobile phone, PDA, tablet, personal computer, etc. In various embodiments, the control device 1318 communicates with the computing system 1300 via a wireless (e.g., antenna 1314 or wireless communication module) connection or a wired connection. As described above, the display device 1316 can be an electronic display attached to the wearable system or distinct from the wearable system (e.g., mobile phone, tablet). The antenna 1314 can facilitate communication and relay commands between the computing system 1300, the display device 1316, and/or the control device 1318.

The techniques introduced herein can be implemented by, for example, programmable circuitry (e.g., one or more microprocessors), programmed with software and/or firmware, entirely in special-purpose hardwired (i.e., non-programmable) circuitry, or in a combination of such forms. Special-purpose circuitry can be in the form of, for example, one or more application-specific integrated circuits (ASICs), programmable logic devices (PLDs), field-programmable gate arrays (FPGAs), etc.

Software or firmware to implement the techniques introduced herein may be stored on a machine-readable storage medium and may be executed by one or more general-purpose or special-purpose programmable microprocessors. A "machine-readable medium," as the term is used herein, includes any mechanism that can store information in a form accessible by a machine (e.g., computer, network device, mobile phone, PDA, manufacturing tool, any device with one or more processors). For example, a machine-accessible medium includes recordable/non-recordable media (e.g., read-only memory (ROM), random access memory (RAM), magnetic disk storage media, optical storage media, flash memory devices).

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

While various embodiments have been described in the context of fully functioning computers and computing systems, those skilled in the art will appreciate that the various embodiments are capable of being distributed as a program product in a variety of forms, and that the disclosure applies equally regardless of the particular type of machine or computer-readable media used to actually effect the distribution.

Although the Detailed Description describes certain embodiments and the best mode contemplated, no matter how detailed the above appears in text, the embodiments can be practiced in many ways. Details of the systems and methods may vary considerably in their implementation details, while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments under the claims.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

The invention claimed is:

1. An apparatus for managing adherence to a medication regimen, the apparatus comprising:
    a wristband configured to be worn on a wrist of a user;
    a first camera coupled to the wristband,
        wherein the first camera is located in an anterior region of the wrist and oriented toward the user's hand;
    a second camera coupled to the wristband, wherein the second camera is located in a posterior region of the wrist and oriented toward the user's hand;
an image projector that is coupled to the wristband,
wherein the image projector is located in the anterior region of the wrist, and
wherein the image projector is configured to project an image onto a surface;
a processor;
a rechargeable power supply that is coupled to the processor and the first and second cameras;
a wireless communication module that establishes a communication channel between the apparatus and a distinct electronic device across a network; and
a storage.

2. The apparatus of claim 1, further comprising:
a motion sensor configured to continually track movement of the apparatus and, activate the first camera, the second camera, or both upon sensing a particular gesture,
wherein the particular gesture corresponds to one of a plurality of gesture records stored in the storage.

3. The apparatus of claim 1, further comprising:
a sound sensor that is sensitive to ambient sound and causes the first camera, the second camera, or both to turn on upon sensing a particular sound,
wherein the particular sound corresponds to one of a plurality of sound records stored in the storage.

4. The apparatus of claim 3, wherein the particular sound is a vocal command from the user.

5. The apparatus of claim 1, further comprising:
a climate sensor that is sensitive to ambient climate conditions and monitors ultraviolet index, humidity, temperature, atmospheric pressure, illuminance level, or any combination thereof.

6. The apparatus of claim 1, wherein the surface is a palm of the user's hand.

7. The apparatus of claim 1, further comprising:
a speaker that audibly projects a reminder, a notification, or an instruction to the user.

8. The apparatus of claim 1, further comprising:
a pressure sensor that is embedded within the wristband and located in the anterior region of the wrist,
wherein the pressure sensor is positioned on an inner side of the wristband to be proximate to the user's wrist, and
wherein the pressure sensor is configured to sense changes in tendon tension along the anterior side of the wrist.

* * * * *